(12) United States Patent
Sclip et al.

(10) Patent No.: US 10,365,217 B2
(45) Date of Patent: Jul. 30, 2019

(54) LIQUID PRESENCE/TURBIDITY SENSOR USING SINGLE OPTICAL CHANNEL

(71) Applicant: ILLINOIS TOOL WORKS INC., Glenview, IL (US)

(72) Inventors: Marco Sclip, Sumirago (IT); Davide Bordignon, Travedona Monate (IT)

(73) Assignee: Illinois Tool Works Inc., Glenview, IL (US)

( * ) Notice: Subject to any disclaimer, the term of this patent is extended or adjusted under 35 U.S.C. 154(b) by 152 days.

(21) Appl. No.: 15/034,968

(22) PCT Filed: Oct. 21, 2014

(86) PCT No.: PCT/US2014/061464
§ 371 (c)(1),
(2) Date: May 6, 2016

(87) PCT Pub. No.: WO2015/073165
PCT Pub. Date: May 21, 2015

(65) Prior Publication Data
US 2016/0274028 A1    Sep. 22, 2016

Related U.S. Application Data

(60) Provisional application No. 61/903,035, filed on Nov. 12, 2013.

(51) Int. Cl.
*G01N 21/53* (2006.01)
*D06F 39/00* (2006.01)
(Continued)

(52) U.S. Cl.
CPC ......... *G01N 21/532* (2013.01); *D06F 39/004* (2013.01); *G01N 21/41* (2013.01);
(Continued)

(58) Field of Classification Search
CPC ...... G01N 21/532; G01N 21/41; G01N 21/59; G01N 21/5907; G01N 21/8507;
(Continued)

(56) References Cited

U.S. PATENT DOCUMENTS

| 4,637,719 A | 1/1987 | Herman |
| 5,083,447 A | 1/1992 | Kiuchi et al. |
| 5,100,226 A * | 3/1992 | Freeman ............... A61F 2/1613 351/159.11 |

(Continued)

FOREIGN PATENT DOCUMENTS

| DE | 102006052892 A1 | 5/2008 |
| EP | 0393311 A1 | 10/1990 |

OTHER PUBLICATIONS

ISR and WO for PCT/US2014/061464 dated Feb. 11, 2015.

*Primary Examiner* — Hina F Ayub
(74) *Attorney, Agent, or Firm* — Boyle Fredrickson, S.C.

(57) ABSTRACT

A multisensor employs an optical system that is modified by the index of refraction of fluid passing between a light emitter and light detector to successfully distinguish between air and water (of any turbidity) and between water of different turbidity values. The optical system may employ lenses contacting the fluid to change their focal length and thus to focus and defocus light on the light detector depending on an index of refraction of the fluid.

14 Claims, 5 Drawing Sheets

(51) Int. Cl.
  *G01N 21/85*   (2006.01)
  *G01N 21/59*   (2006.01)
  *G01N 21/41*   (2006.01)
  *A47L 15/42*   (2006.01)
  *D06F 33/02*   (2006.01)

(52) U.S. Cl.
  CPC ........... *G01N 21/534* (2013.01); *G01N 21/59* (2013.01); *G01N 21/5907* (2013.01); *G01N 21/8507* (2013.01); *A47L 15/4297* (2013.01); *D06F 33/02* (2013.01); *D06F 2202/02* (2013.01); *D06F 2204/04* (2013.01); *D06F 2204/08* (2013.01); *G01N 2201/062* (2013.01); *G01N 2201/0638* (2013.01)

(58) Field of Classification Search
  CPC ...... G01N 2201/062; G01N 2201/0638; D06F 39/004; D06F 33/20; D06F 2202/02; D06F 2204/04; D06F 2204/08; A47L 15/5297
  USPC ........................................................ 356/442
  See application file for complete search history.

(56) References Cited

U.S. PATENT DOCUMENTS

| | | | |
|---|---|---|---|
| 2006/0060762 A1* | 3/2006 | Chan | H04M 1/605 250/221 |
| 2007/0151584 A1 | 7/2007 | Omachi et al. | |
| 2013/0092189 A1 | 4/2013 | Tang | |
| 2013/0342930 A1* | 12/2013 | Mahnad | G11B 15/602 360/31 |

* cited by examiner

LIQUID PRESENCE/TURBIDITY SENSOR USING SINGLE OPTICAL CHANNEL

CROSS-REFERENCE TO RELATED APPLICATIONS

This application is a National Phase of International Application No. PCT/US2014/061464, filed Oct. 21, 2014, and claims the benefit of US provisional application 61/903,035 filed Nov. 12, 2013, and hereby incorporated by reference.

FIELD OF THE INVENTION

The present invention relates to optical sensors for the measurement of both of the turbidity of liquid and the presence of the liquid in a sensing volume and in particular to an optical sensor that may make both measurements using a single optical channel.

BACKGROUND OF THE INVENTION

Optical sensors may be used to detect the presence or absence of a liquid, for example, in a washing machine or dishwasher and for determining the turbidity of that liquid when liquid is present. Such turbidity measurements may indicate the amount of dirt suspended in the water and may be used to assess how much cleaning or rinsing is required.

The turbidity of a liquid in a sampling volume may be measured by assessing how much light passes between a light transmitter and light detector positioned so that the path of light between the light transmitter and light detector crosses the sampling volume. The light transmitter may be an electronic light source such as a light emitting diode and the light detector may be an electronic light sensor such as a photodiode, phototransistor, or the like.

The amount of light passing between the light transmitter and light detector in a turbidity sensor will also be affected by whether the sampling volume contains air or water. Air in the sampling volume will typically reduce the amount of light passing between the light transmitter and light detector when compared to the light transmitted by a clear liquid. This is because the turbidity sensor normally includes optical elements configured to maximize light transmission in liquid to ensure sufficient light is transmitted for measurement of highly turbid water. As a result, a turbidity sensor with a single optical channel (for example, one light transmitter and one light detector) cannot reliably distinguish between air and turbid water.

Multisensors which combine a liquid presence sensor and a turbidity sensor normally use two optical channels each producing independent signals. The first channel may provide a straight transmission path through the sampling volume between a first light transmitter/receiver pair to deduce turbidity. The second channel may provide a transmission path reflecting off a boundary between an optical element and material in the sampling volume between the second light transmitter/receiver pair. The optical element will provide for a greater internal reflection when air is in the sampling volume than when water is in the sampling volume thus reliably distinguishing between air and liquid.

These two optical channels may share one of optical transmitters or receivers, for example, through multiplexing techniques, but generally require at least three components selected from optical transmitters and receivers and two optical paths.

SUMMARY OF THE INVENTION

The present inventors have recognized that a single optical channel can be used to detect turbidity and to detect the presence or absence of liquid by ensuring that the attenuation of the light in this optical channel is less for air than it is for clear water. In one embodiment, this relative attenuation is enforced by focusing the light between the light transmitter and the light detector using refractive elements under the assumption that the refractive elements are in an air environment. The introduction of water into that environment upsets this assumption and de-focuses these refractive elements reducing the light intensity at the light detector.

Specifically then, at least one embodiment of the invention provides a turbidity sensor having an electronic light source and electronic light detector positioned in opposition along an optical path through a channel open to receive a passage of fluid therethrough. At least one optical element is positioned along the optical path in contact with the fluid to change the transmission of light between the electronic light source and electronic light detector as a function of an index of refraction of the fluid relative to material of the optical element to produce a first level of transmission of light from the electronic light source to the electronic light detector when the fluid in the passage is air and to produce a second level of transmission of light from the electronic light source to the electronic light detector when the fluid in the passage is clear water, the first level being greater than the second level.

It is thus a feature of at least one embodiment of the invention to provide a turbidity sensor that unambiguously distinguishes between air and water of different turbidities.

The optical element may be a focusing lens positioned along the optical path to be in contact with fluid in the passage.

It is thus a feature of at least one embodiment of the invention to employ optical elements that increase the light energy transmitted through the fluid by focusing.

The turbidity sensor may employ two lenses positioned along the optical path to be in contact with fluid from the passage wherein the lenses are positioned and focused to provide the first level of transmission of light from the electronic light source to the electronic light detector when the fluid in the passage is air and the second level of transmission of light from the electronic light source to the electronic light detector when the fluid in the passage is clear water, the first level of transmission of light being greater than the second level of transmission of light.

It is thus a feature of at least one embodiment of the invention to employ a defocusing to distinguish between types of fluid in contrast to fluid turbidities.

The lenses may be circular lenses selected from the group consisting of circular plano-convex lenses and bi-convex lenses.

It is thus a feature of at least one embodiment of the invention to permit the use of common lens structures.

Alternatively, the lenses may be cylindrical or spherocylindrical lenses.

It is thus a feature of at least one embodiment of the invention to provide a lens structure that permits wide beam shapes or that accommodates optical misalignment.

The turbidity sensor may include detection circuitry for detecting at least three levels of light transmission corresponding to the fluid in the passage being air, the fluid in the passage being water of low turbidity and the fluid in the passage being water of high turbidity, higher than the low turbidity.

It is thus a feature of at least one embodiment of the invention to provide a turbidity sensor that may be used for multiple control purposes within the appliance to both sense turbidity and distinguish between different fluids.

The turbidity sensor may include only a single electronic light source and single electronic light detector.

It is thus a feature of at least one embodiment of the invention to greatly reduced the parts count required of current turbidity sensor technologies.

Other features and advantages of the invention will become apparent to those skilled in the art upon review of the following detailed description, claims and drawings in which like numerals are used to designate like features.

Figure 1:
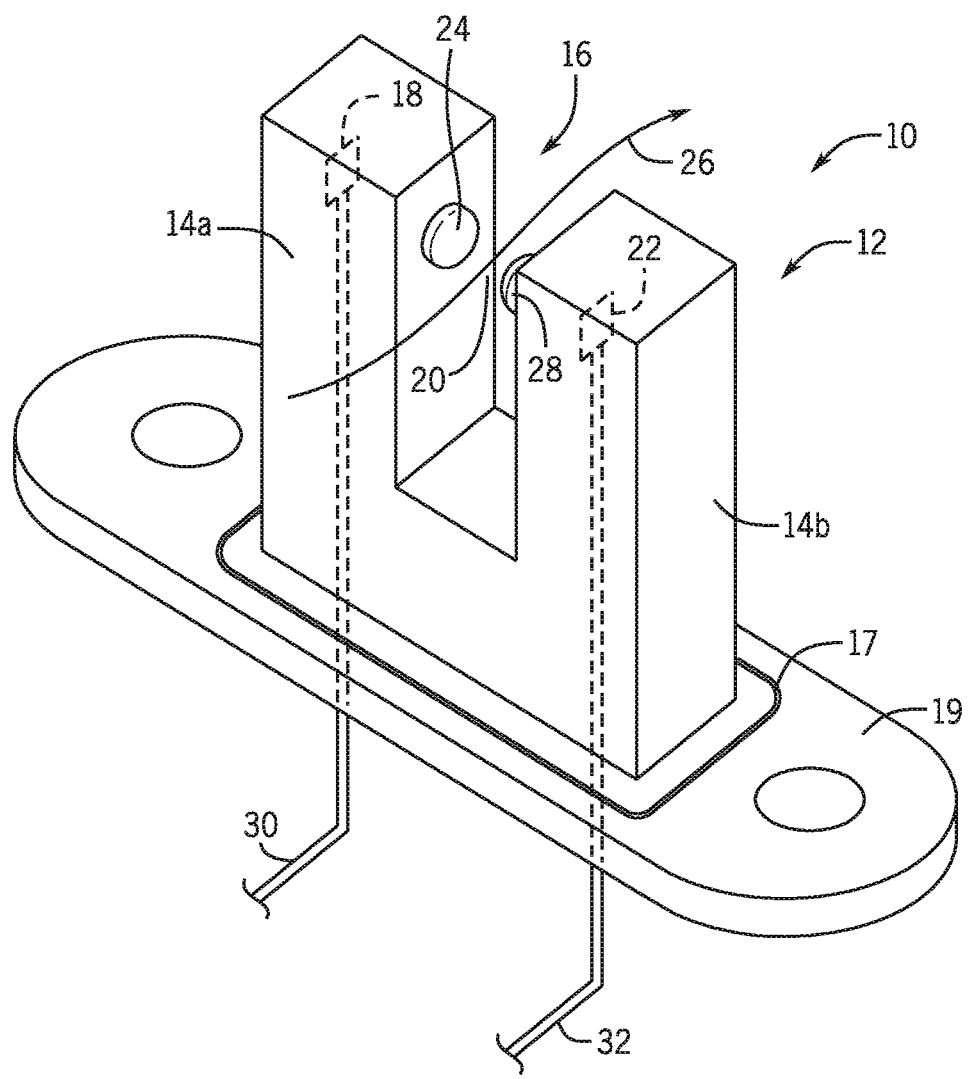
FIG. 1 is a simplified perspective view of a multisensor in phantom detecting both turbidity and liquid presence constructed according to one embodiment of the invention.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE PREFERRED EMBODIMENTS

Referring now to FIG. 1, a multisensor 10 per the present invention may provide a U-shaped frame 12 having opposed arms 14a and 14b extending in opposition across a fluid passage 16. The first arm 14a may hold at a distal end a light transmitter 18, for example, providing a light source, and including but not limited to a light emitting diode die or light emitting diode die plus encapsulating lens element. The light transmitter 18 directs light along optical axis 20 through the fluid passage 16 toward a distal end of the second arm 14b.

The second arm 14b may in turn hold at a distal end a light detector 22, for example, a photosensor such as a photodiode, photo transistor, a photo resistor, or photocell, receiving light along the optical axis 20 through the fluid passage 16 from the first arms 14a. The photosensor may include some integrated optical lenses or may be a die without lens.

A collimating lens 24 may be positioned along the optical axis 20 between the light transmitter 18 within the arm 14a and an external fluid 26 in the fluid passage 16. Likewise a focusing lens 28 may be positioned along the optical axis 20 between the external fluid 26 in the fluid passage 16 and the light detector 22 in the arm 14b.

Generally both the collimating lens 24 and focusing lens 28 will contact the external fluid 26 such as may modify the focal properties of the collimating lens 24 and the focusing lens 28 by changing the difference in index of refraction between the optical material of the lenses 24 and 28 and the surrounding medium such as changes refraction.

The light transmitter 18 may communicate via leads 30 passing within the arm 14a to a source of electrical power and the light detector 22 may communicate via leads 32 passing within the arm 14b to detection circuitry for determining an amount of light received by the light detector 22.

The collimating lens 24 and the focusing lens 28 may be sealed to the respective arms 14a and 14b to prevent fluid from leaking into the arms 14 which are otherwise sealed against fluid ingress. The arms 14 may attach to a base 19 that includes a seal 17 allowing the base 19 to be attached through an opening and sealed to the opening in a channel containing a stream of liquid flow of external liquid 26 to prevent leakage therefrom so that the arms 14 extend into the liquid flow and the leads 30 and 32 are accessible outside of the channel from an opposite side of the base 19.

Figure 2:
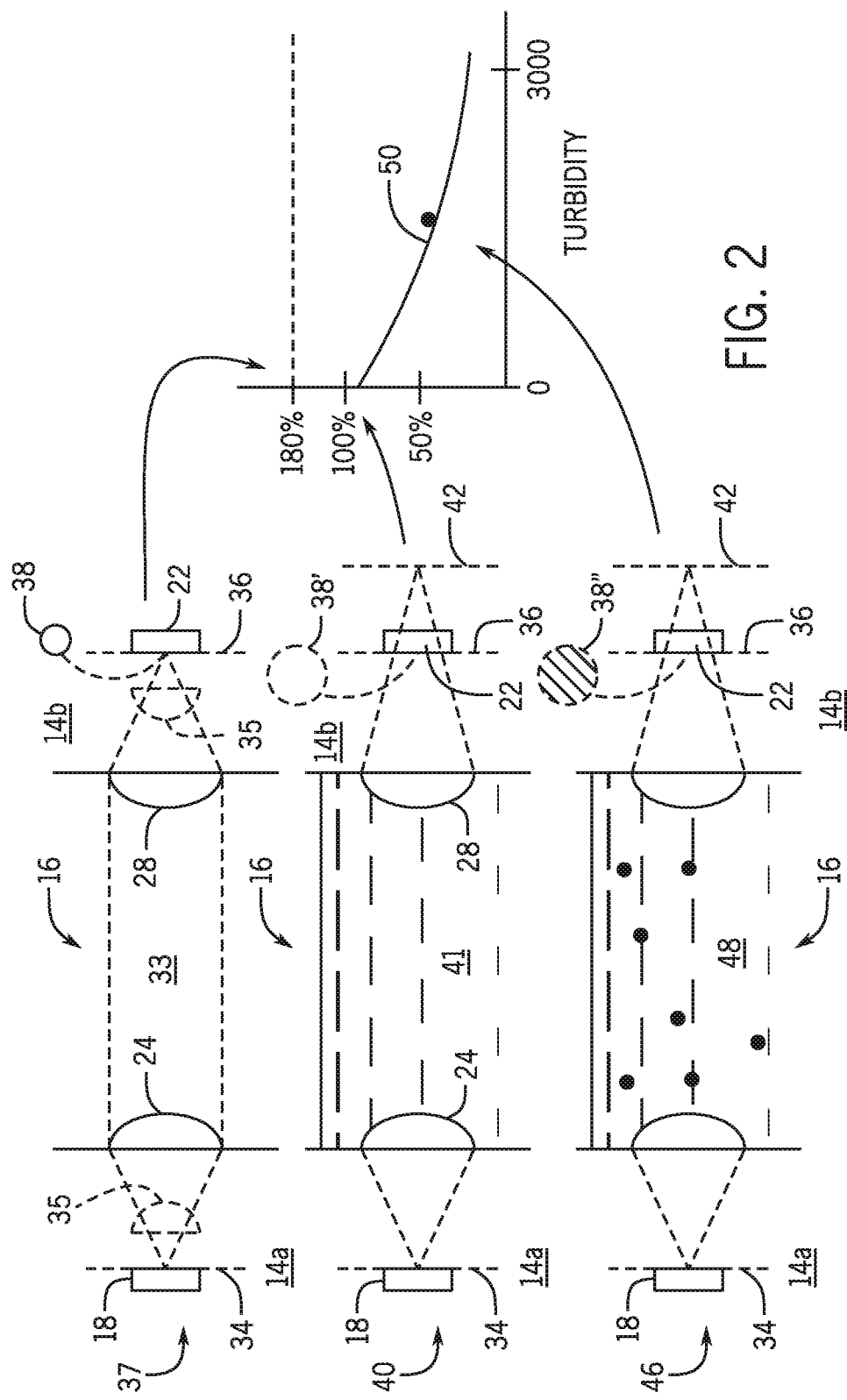
FIG. 2 is a depiction of the optical path of the sensor of FIG. 1 under three conditions of air, clear water, and turbid water interposed between the light transmitter and light detector and showing a relative signal strength provided by the multisensor in each situation.

Referring now to FIG. 2, in environment 37 when the multisensor 10 is operated with air 33 within the fluid passage 16, collimating lens 24 and focusing lens 28 transmit an image of a surface of the light transmitter 18 originating at a first focal plane 34 to a second focal plane 36 focused on the surface of the light detector 22. In this regard, collimating lens 24, focusing lens 28, and the geometry of the focal planes 34 and 36 and the positions of the lenses 24 and 28 are selected according to well understood optical principles to provide this focusing with air 33 within the fluid passage 16.

It will be understood that this focusing described above is dependent on the focal length of the lenses 24 and 28, the latter of which is generally determined by the difference between the index of refraction of the lens material and the index of refraction of the medium surrounding the lens and in particular the media in the fluid passage 16.

Figure 5:
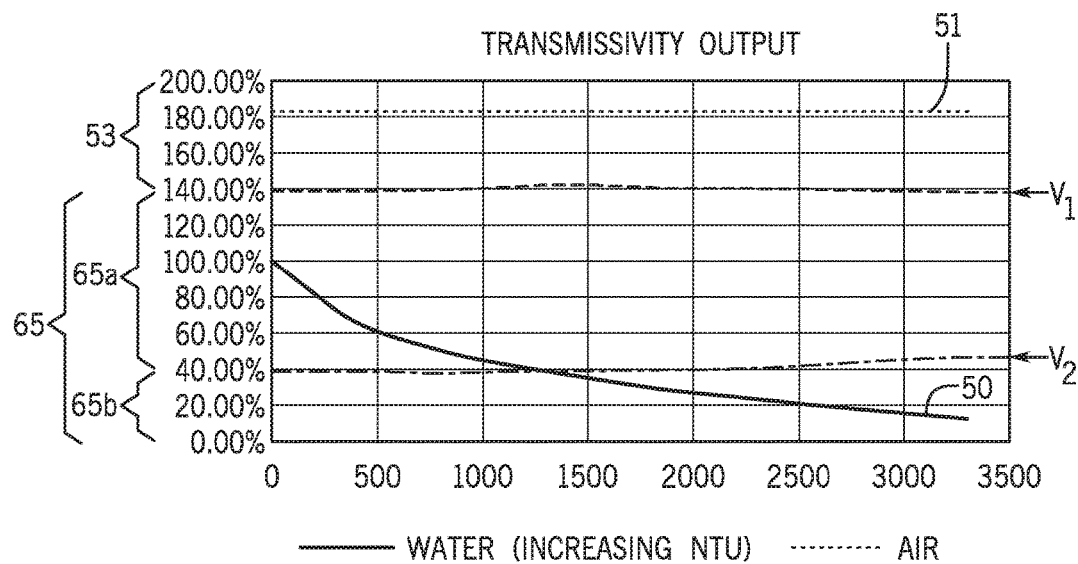
FIG. 5 is a chart similar to that of FIG. 4 showing the separation of transmission levels for air and water in the present invention.

By placing light detector 22 at focal plane 36 of lens 28 in the environment 37, a compact illumination spot 38 (shown displaced from light detector 22 and rotated 90 degrees for clarity) will generally conform to an image of the light transmitter 18 concentrating and maximizing the light energy from the light transmitter 18 on the active area of the light detector 22. This will produce a detector output, for example, of 180 percent, as referenced to a detector output of 100 percent expected when clear liquid water is within the fluid passage 16 as shown in FIG. 5 by curve 51. This output is independent of the turbidity of water (shown in the horizontal axis of FIG. 5) simply because water is not positioned between the light transmitter 18 and the light detector 22 in this environment 37.

Referring still to FIG. 2, in environment 40, when the multisensor 10 is operated with clear water 41 within the fluid passage 16, collimating lens 24 and focusing lens 28 transmit an image of a surface of the light transmitter 18 at a second focal plane 42 past the surface of the light detector 22. In this case, the illumination spot 38' on the light detector 22 will be an unfocused image of the light transmitter 18 and thus be larger to extend outside the boundaries of the light detector 22 and more diffuse within the boundaries of the light detector 22, reducing the amount of light detected by the light detector 22 to a value of 100 percent (normalized to this water transmission path) which is, importantly, lower than that obtained when air 33 is within the fluid passage 16 as shown in environment 37.

Finally, referring to FIG. 2, in environment 46, when multisensor 10 is operated with turbid water 48 within fluid passage 16, including, for example, water holding suspended solids and bubbles, collimating lens 24 and focusing lens 28 again focus the image of the surface of the light transmitter 18 at second focal plane 42 removed from the light detector 22 providing not only a more diffuse illumination spot 38" but also one that is attenuated by the scattering and absorption of the turbid water 48. The result is a detector value, for example, of 50 percent, being below the detector values for air or clear water. Generally, a range of varying turbidity will provide a corresponding range of varying attenuation in detected light along a curve 50 in a plot of light attenuation vs. turbidity that may be used to provide a quantitative output of turbidity.

Figure 4:
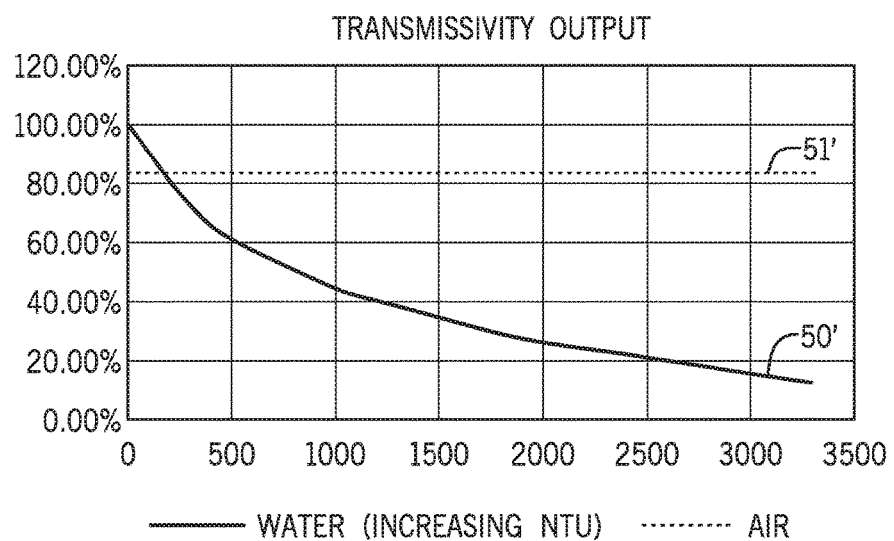
FIG. 4 is a chart of light transmission in the prior art showing the overlap of light transmission levels for air and water normalized to a peak value of 100 percent and plotted against turbidity in Nephelometric Turbidity Units (NTU)

The chart shown in FIG. 5 may be contrasted with the chart in FIG. 4 showing a prior art system without the focused optics of the present invention such as produces an overlap between curve 51' corresponding to curve 51 and curve 50' corresponding to curve 50. In the chart of FIG. 4, the presence of air between the light transmitter 18 and light detector 22 cannot be distinguished from the presence of water between the light transmitter 18 and the light detector 22 if the water has an NTU value of approximately 200. Given that there will be some variation in the values of the signals based on normal manufacturing tolerances, the practical effect is that the presence of air or water may not be adequately distinguish over an important range of turbidity. In contrast, the chart of FIG. 5 shows that the presence of air may be readily distinguished from the presence of water at all turbidity levels.

Referring still to FIG. 2, it will be noted that the light transmitter 18 and light detector 22 may include optional ancillary lenses 35, for example, incorporated into the packages of the light transmitter 18 and/or light detector 22 or other lenses may be placed along the optical path. Generally these lenses will not be in contact with fluid in the fluid passage 16. The focusing effect of these ancillary lenses 35 is simply accommodated in the placement and focusing of the lenses 24 and 28 to provide the desired detection effect described above.

Figure 3A:
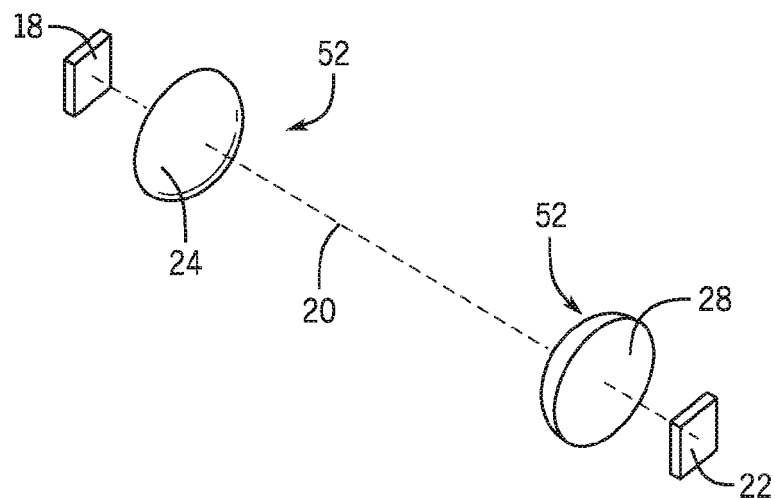
FIGS. 3a-3c are examples of three different optical systems that may be employed in various embodiments of the present invention.
Figure 3B:
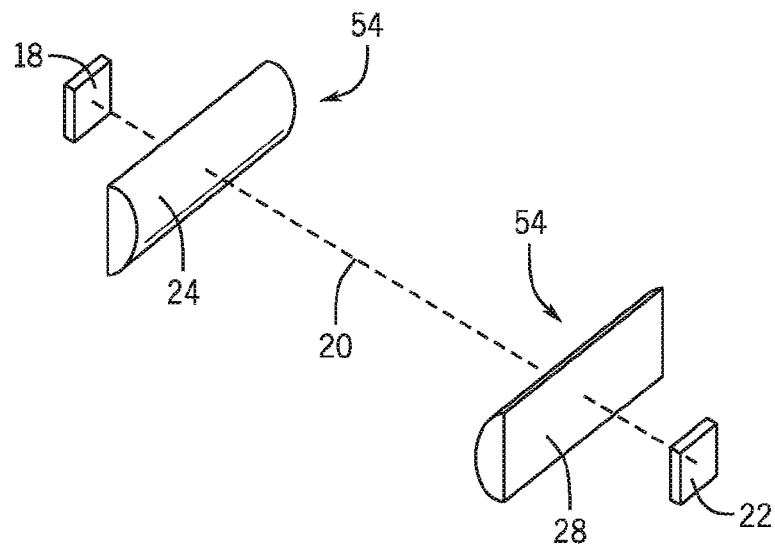
Figure 3C:
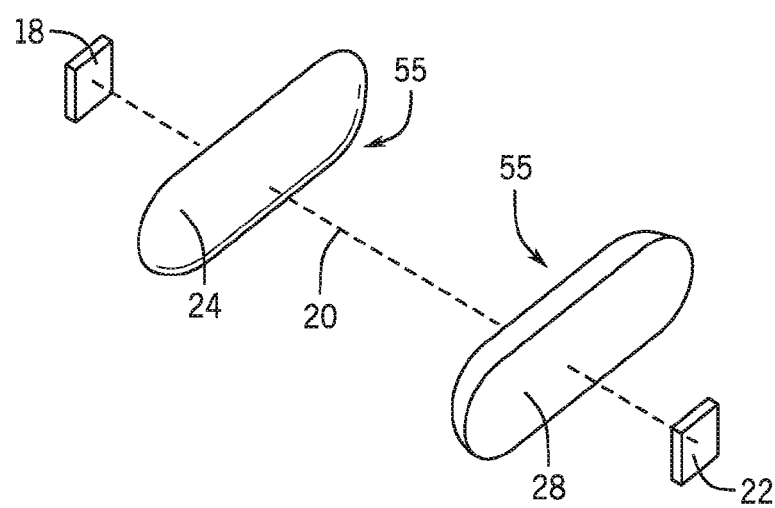

Referring now to FIG. 3, various optical systems may be used in the present invention including circular planoconvex lenses or biconvex lenses 52 as shown in FIG. 3a, cylindrical lenses 54 as shown in FIG. 3b and spherocylindrical lenses 55 as shown in FIG. 3c. A cylindrical lens 54 is one having a surface that is a portion of a cylinder. A sphero-cylindrical lens 55 is one having different portions of its surface that are portions of spheres (for example, the ends of the lens) and other portions that are portions of a cylinder. Any of these lenses may be solid surface or Fresnel versions. It is contemplated that the lenses will be injection molded but other fabrication techniques may be employed. The lenses may be integrally molded into opposed faces of the arms 14.

Each of these lenses 52, 54, and 55 may be configured to provide a concentrated focusing of light from the light transmitter 18 on the light detector 22, and thus a maximum light detected at light detector 22 in the presence of air along the optical axis 20, and a lesser focusing and lower light detected at light detector 22 even with perfectly clear water and decreasing with increased water turbidity.

Figure 6:
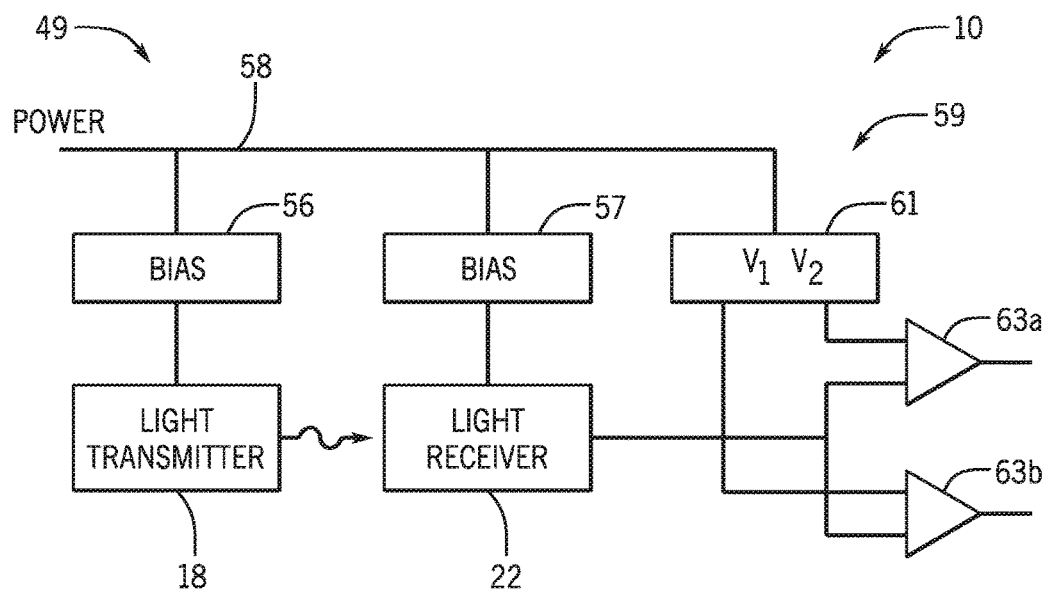
FIG. 6 is a simplified block diagram of detection circuitry suitable for use with the present invention.

Referring now to FIG. 6, a control circuit 49 suitable for the present sensor may provide for a biasing circuit 56 for the light transmitter 18 and a biasing circuit 57 for the light detector 22 both operating from a common power line 58. Fluctuations in the power, for example, incident to unregulated power in a home appliance or the like may be accommodated by also providing a comparator system 59 that generates threshold voltages 61 from the power line 58. In this way, common mode variations in the power line 88 cause the threshold voltages to rise and fall together with the biasing of the light transmitter 18 and light detector 22 to offset this effect. The generated threshold voltages may provide for two threshold voltages $V_1$ and $V_2$ provided to separate comparators 63a and 63b which also receive an output from the light detector.

Referring momentarily to FIG. 5, these threshold voltages $V_1$ and $V_2$ may distinguish curve 51 from curve 50 at all turbidities and distinguish a high and low turbidity value on curve 50 such as may trigger a washing process. Specifically, the voltage $V_1$ defines above it, a first range 53 of light transmission indicative of the presence of air between the light transmitter 18 and light detector 22, and the voltage $V_1$ defines below it a second range 65 associated only with the presence of water between the light transmitter 18 and light detector 22. The voltage $V_2$ divides the second range 65 into a first sub range 65a associated with a first turbidity and the second sub range 65b associated with a second turbidity. These first and second sub ranges 65a and 65b may be used to control the washing cycles of the appliance selecting between light and heavy cycles while the first range 53 may be used to determine that the water is present or absent at the beginning or end of the cycles to ensure that a washing chamber is filled or emptied as the case may be.

Figure 7:
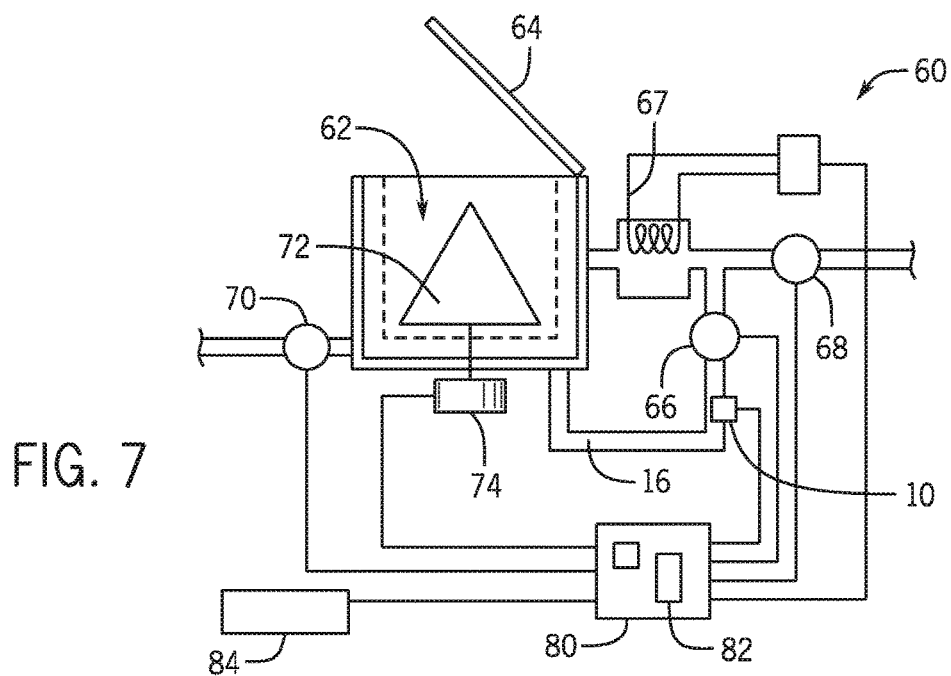
FIG. 7 is a simplified diagram of a washing appliance that may use the multisensor of the present invention.

Referring now to FIG. 7, the multisensor 10 of the present invention may be positioned in a fluid conduit as part of a washing appliance 60 having a washing chamber 62 accessible through a lid 64. Washing water may be circulated to the washing chamber 62 as pumped by a pump 66 through the fluid passage 16. The appliance may include water heater 67 for heating that recirculating water, water inlet valve 68 for adding water from a public water supply to the washing chamber 62, drain valve 70 for removing water from the washing chamber 62 into a water drain, and agitator 72 for agitating the water within the washing chamber as connected to a motor 74. Generally each of the multisensor 10, pump 66, water heater 67, valve 68, valve 70, and motor 74 may be read by or controlled by electronic computer 80 executing a stored program 82 to adjust washing parameters based on turbidity and the presence or absence of water within the fluid passage 16. The computer 80 may communicate with a console control 84 providing input and output to a user of the appliance. For example, the multisensor 10 may determine how dirty is the material being washed and change the length or number of washing cycles by controlling duration of operation of the pump 66 or the temperature of the water by controlling the duration of the operation of the heater 67.

It will be appreciated that the invention may also be accomplished with a single lens system, for example, providing a lens only at the light detector so long as the same defocusing occurs in the presence of liquid between the light transmitter and light detector. In one embodiment, a single light detector and single light sensor may be used, as shown herein; however, will be appreciated that multiple light sensors and light detectors may be added in tandem for increased sensitivity while still constituting a single optical channel. The invention may also be used with completely separate optical channels yet still provide an optical system that maximizes light throughput on one channel for air over water. The path of light along the optical axis 20 within the arms 14a and 14b may travel through air, although any medium of known index of refraction may be placed in this region.

While the present invention has been described with respect to a U-shaped frame 12, it will be appreciated that the fluid passage 16 may be of arbitrary shape that allows the flow of external fluid 26 between the light transmitter 18 and the light detector 22 including, for example, a tubular structure.

Various features of the invention are set forth in the following claims. It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

What is claimed is:

1. A multisensor comprising:
an electronic light source and electronic light detector positioned at ends of an optical path through a channel open to receive a passage of fluid therethrough, the electronic light detector providing an electrical output signal; and
at least one optical element positioned along the optical path and to be positioned within the channel and adapted to contact the fluid in the channel to change a transmission of light between the electronic light source and electronic light detector as a function of an index of refraction of the fluid relative to material of the optical element to produce a first level of transmission of light from the electronic light source to the electronic light detector and a first value of an electrical output signal when the fluid in the passage is air and to produce a second level of transmission of light from the electronic light source to the electronic light detector and a second value of the electrical output signal detector when the fluid in the passage is clear water, the first level being greater than the second level and indicating a greater transmission of light to the electronic light detector;
wherein the multisensor further comprises detection circuitry for detecting at least three levels of light transmission corresponding to the fluid in the passage being air, the fluid in the passage being water of low turbidity, and the fluid in the passage being water of high turbidity higher than the low turbidity;
wherein the detection circuitry further comprises comparison circuitry comparing the electrical output signal to a first threshold level distinguishing between air and water where air provides greater transmission of light to the electronic light detector and comparing the electrical output signal to a second threshold level distinguishing between clear water and turbid water where clear water provides greater transmission of light to the electronic light sensor.

2. The multisensor of claim 1 wherein the optical element is a focusing lens positioned along the optical path to be in contact with fluid in the passage.

3. The multisensor of claim 2 wherein the at least one lens is two lenses positioned along the optical path to be in contact with fluid from the passage wherein the lenses are positioned and focused to provide the first level of transmission of light from the electronic light source to the electronic light detector when the fluid in the passage is air and the second level of transmission of light from the electronic light source to the electronic light detector when the fluid in the passage is clear water, the first level of transmission of light being greater than the second level of transmission of light.

4. The multisensor of claim 3 wherein the lenses are circular lenses selected from the group consisting of circular, plano-convex lenses and bi-convex lenses.

5. The multisensor of claim 3 wherein the lenses are cylindrical lenses.

6. The multisensor of claim 3 wherein the lenses are sphero-cylindrical lenses.

7. The multisensor of claim 3 wherein the two lenses and the electronic light source and electronic light detector are supported by arms of a U-shaped channel to also hold electrical conductors associated with the electronic light source and electronic light detector extending through the arms to a base joining the arms.

8. The multisensor of claim 7 including a watertight housing and wherein at least one lens is sealed to the housing to prevent water ingress into the housing past at least one lens and wherein the electronic light detector and electronic light source are contained within the housing.

9. The multisensor of claim 1 wherein the electronic light source is a light emitting diode.

10. The multisensor of claim 1 wherein the electronic light detector is selected from the group consisting of a photo diode, a photo transistor, a photocell, and a photo resistor.

11. The multisensor of claim 1 further including additional lenses in the optical path.

12. The multisensor of claim 11 wherein the additional lenses are integrated with at least one of the electronic light source and electronic light detector.

13. The multisensor of claim 1 comprising only a single electronic light source and single electronic light detector.

14. The multisensor of claim 1 wherein the optical path is a substantially straight line with light passing along a single direction.

* * * * *